(12) United States Patent
Taylor et al.

(10) Patent No.: US 6,682,893 B2
(45) Date of Patent: Jan. 27, 2004

(54) GEL PAD ARRAYS AND METHODS AND SYSTEMS FOR MAKING THEM

(76) Inventors: Seth Taylor, 100 Memorial Dr. Apt. 2-9B, Cambridge, MA (US) 02142; Kevin Croker, 1271 Lilac Ct., Cheshire, CT (US) 06410-3658; Shane Weber, 1 Evergreen Dr., Woodbridge, CT (US) 06525-1025

( * ) Notice: Subject to any disclaimer, the term of this patent is extended or adjusted under 35 U.S.C. 154(b) by 0 days.

(21) Appl. No.: 09/934,420

(22) Filed: Aug. 21, 2001

(65) Prior Publication Data

US 2002/0001813 A1 Jan. 3, 2002

Related U.S. Application Data

(63) Continuation of application No. 09/234,288, filed on Jan. 20, 1999.
(60) Provisional application No. 60/075,698, filed on Jan. 21, 1998, provisional application No. 60/071,980, filed on Jan. 20, 1998, and provisional application No. 60/072,089, filed on Jan. 21, 1998.

(51) Int. Cl.[7] .............................. C12Q 1/68; A61K 9/14; G01N 33/566; C07H 21/04
(52) U.S. Cl. ........................... 435/6; 424/488; 424/486; 436/501; 536/23.1
(58) Field of Search .................... 435/6, 91.2; 436/501; 536/126, 23.1, 24.3, 24.33; 424/488, 486, 487

(56) References Cited

U.S. PATENT DOCUMENTS

| | | | |
|---|---|---|---|
| 5,143,854 A | * | 9/1992 | Pirrung et al. ............... 435/516 |
| 5,552,270 A | * | 9/1996 | Khrapko et al. ................ 435/6 |
| 5,800,421 A | * | 9/1998 | Lemelson ................ 604/891.1 |
| 5,840,338 A | * | 11/1998 | Roos et al. .................. 424/468 |

OTHER PUBLICATIONS

Yershov et al. DNA analysis and diagnostics on oligonucleotide microchips. Proc. Natl. Acad. Sci. USA. vol. 93, pp. 4913–4918.*

Kaetsu et al. Immobilization and Culture of Cells. Annals of the New York Academy of Sciences. 613, pp. 781–785.*

\* cited by examiner

*Primary Examiner*—Kenneth R. Horlick
*Assistant Examiner*—Cynthia Wilder
(74) *Attorney, Agent, or Firm*—Fish & Richardson P.C.

(57) ABSTRACT

Gel pads and gel pad arrays, and methods for making and using them, are disclosed. The gel pads preferably comprise an intelligent gel.

25 Claims, 5 Drawing Sheets

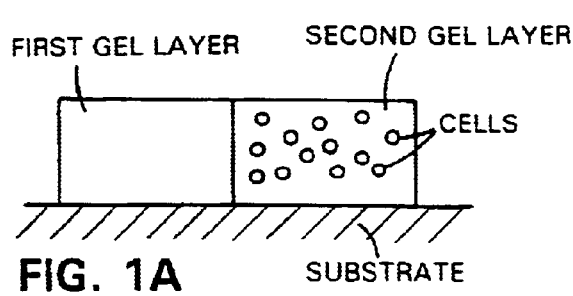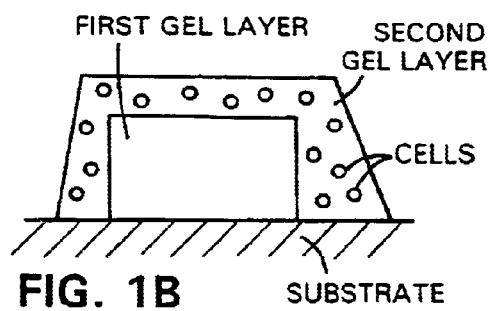
FIG. 1A  FIG. 1B
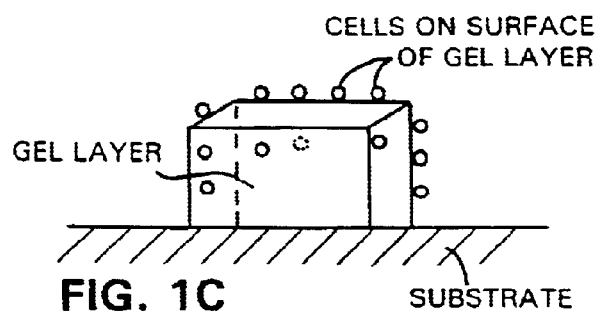
FIG. 1C

GEL PAD ARRAYS AND METHODS AND SYSTEMS FOR MAKING THEM

RELATED APPLICATIONS

This application is a continuation of Ser. No. 09/234,288 filed on Jan. 20, 1999 which is a continuation-in-part of U.S. Provisional Serial No. 60/075,698, filed Jan. 21, 1998; U.S. Provisional Serial No. 60/071,980, filed Jan. 20, 1998; and U.S. Provisional Serial No. 60/072,089, filed Jan. 21, 1998. The contents of each of these provisional patent applications is hereby incorporated by reference.

BACKGROUND OF THE INVENTION

Rapid advances in the ability to accurately determine polynucleotide sequences, such as DNAs and RNAs from the genomes of organisms, has made possible the sequencing of huge quantities of polynucleotides. In recent years, the entire genomes of microorganisms, such as *Helicobacter pylori*, have been sequenced.

Traditional sequencing methods have relied on automated sequencing equipment which processes a polynucleotide strand one base at a time. A more recent approach, sequencing by hybridization (SBH), which could potentially increase sequencing throughput, relies on fragmenting a target polynucleotide into short segments; these short segments can be captured, for example on an ordered microarray of immobilized complementary single-stranded DNA probes, and the sequences of the target polynucleotide determined by analyzing the overlap of the sequences of the DNA probes bound to fragments of the target polynucleotide. See, for example, U.S. Pat. No. 5,525,464 to Drmanac et al. Microarrays of DNA attached to a solid support have been prepared, see, for example, U.S. Pat. No. 5,445,934 to Fodor et al.

Often, however, DNA microarrays are limited to analyzing nucleic acids in a single, fluid environment. An alternative to conventional DNA microarrays on a solid support is a microarray comprising biological molecules, such as DNA, attached to a matrix of crosslinked polymers known as gel pads. See, e.g., U.S. Pat. No. 5,552,270 to Khrapko et al. Gel pads provide the ability to customize the microenvironment surrounding the DNA in each individual gel pad, which makes possible more sophisticated experiments in micro-array format.

However, although gel pads have certain advantages over convention micro-arrays, new types of arrays, and methods for making them, are needed.

SUMMARY OF THE INVENTION

This invention features gel pad arrays, e.g., arrays on a support, and methods for making and using them. The arrays can be used for sequencing by hybridization (e.g., where the pads include nucleic acid strands immobilized within the gel matrix), for cell based assays (e.g., where the pads include, or are adjacent to and contacting, living cells), and for other uses which will be apparent to one of ordinary skill in the art.

In general, the invention features, a method of providing a gel having a substance disposed within the gel. The method includes:

(1) providing a substrate on which is disposed a gel, e.g., a gel pad or an array of gel pads, and wherein said gel is an intelligent gel, capable of existing in an expanded and a contracted state;

(2) contacting the intelligent gel, while in the expanded state, with the substance, e.g., a solute in a solution, and allowing the substance to enter the gel;

(3) causing the expanded intelligent gel to contract, wherein upon contraction molecules of the substance remain in the gel, thereby forming a gel having a substance disposed, e.g., concentrated or captured, within the gel.

In a preferred embodiment the substance can be: a nucleic acid, e.g., DNA, RNA, or a probe; a protein, e.g., an enzyme which modifies DNA, e.g., DNA polymerase; a particle; a cell; or a reactant.

Substances which can be disposed within a gel can include the following:

A molecule that is important for cell function, for example: a molecule that mediates the expression of specific genes, e.g., hormones, e.g., glucocorticoids; DNA subunits, e.g., nucleotides, e.g., dideoxy nucleotides; a molecule that donates a phosphate group, e.g., ATP; a carbohydrate; a protein; a nucleic acid; a lipid, e.g., a structure based in whole or in part on lipids, e.g., bilayer membrane;

A protein that is generated by a living cell, for example: a protein that interacts with the promoter of a gene, e.g., a transcription factor; a protein that interacts with the origin of replication, e.g., single-strand DNA binding protein; a protein associated with the cytoskeleton of a cell e.g., a matrix attachment protein; a protein associated with the membrane of a cell, e.g., a cell surface receptor; a protein associated with signal transduction pathways within a cell, e.g., the RAS family of proteins; a protein associated with RNA, e.g., heteronuclear RNA binding protein (hnRNP); a protein associated with an immune response, e.g., an antibody; a protein associated with the contraction of muscle, e.g., actin or myosin; a protein that is associated with the chromatin of a cell, e.g., a histone; a protein that mediates protein folding, e.g., a chaperone; a protein associated with cell cycle regulation, e.g., cyclin A;

Enzymes that are generated by living cells, for example: an enzyme that links two nucleic acid molecules together, e.g., a DNA or RNA ligase; an enzyme that cuts nucleic acids, e.g., a restriction enzyme that cuts DNA at the binding site (e.g. EcoR1), a type IIS restriction enzyme that cuts DNA 5' or 3' to the binding site (e.g.); an enzyme that modifies the linking number of a closed circular dsDNA molecule, e.g., a topoisomerase; an enzyme that modifies the ends of a chromosome, e.g., a telomerase; an enzyme comprised in whole or in part of RNA, e.g., a ribozyme; an enzyme that generates proteins from amino acid sububits, e.g., a ribosome; an enzyme that transfers phosphate groups onto a protein, e.g., a kinase; an enzyme that removes a phosphate from a protein, e.g., a dephosphorylase; an enzyme that generates a strand of RNA from a template nucleic acid, e.g., an RNA polymerase; an enzyme that generates a strand of DNA from a nucleic acid template, e.g., a DNA polymerase or a reverse transcriptase; an enzyme that functions as part of the DNA repair process, e.g., an enzyme that modifies mismatched base pairs in double-stranded DNA, e.g., an endonuclease or an exonuclease;

Cells, e.g., cells that can be cultured in vitro, for example, living cells, e.g., bacterial cells, e.g., bacterial cells that cause disease in humans (e.g. *Stapholococcus Aureus, E. coli*); living cells, e.g., eukaryotic cells, e.g., fungal cells, e.g., yeast; living cells, e.g., eukaryotic cells, e.g., mammalian cells, e.g., human cells, e.g., colon cancer cell, e.g., human cell lines derived from colon cancer cells, e.g., colo320 cells; cells useful in this assay include cells from nematodes, e.g., *C. elegans;* flies, e.g., *D. melanogaster;* mouse, e.g., laboratory strains of mouse; rat, e.g., laboratory strains of rat; chicken; cow; bovine; fish, e.g., zebra fish; feline, e.g., house cat; canine; rabbit, e.g., laboratory strains of rabbit; frogs, e.g., *Xenopus laevis;* primates, e.g., humans or monkeys;

In preferred embodiments these cells will be modified with a foreign piece of DNA, e.g., a foreign DNA that incorporates itself into genomic DNA through the process of cloning. In other embodiments, foreign DNA enters the cell but is not incorporated into genomic DNA, e.g., the foreign DNA independently replicates in the cytosol, e.g., a plasmid. For example, the cells are modified with a foreign DNA that codes for a selective factor, e.g., a protein that enables the cell to resist a toxic chemical, e.g., an antibiotic, e.g., beta lactamase. Alternatively, the foreign DNA codes for a recombinant molecule, e.g., a recombinant protein, e.g., a fusion protein, e.g., an expressed fusion protein that contains a tag at one end of the molecule, e.g., a FLAG tag (Asp-Tyr-Lys-Asp-Asp-Asp-Asp-Lys) or a repeat of the amino acid histidine (i.e. HIS tag) for capture of the recombinant protein. Alternatively, the foreign DNA codes for a molecule that imparts a property to the cell e.g., a nutritive property, e.g., the ability of the cell to grow in the absence of a molecule, such as an amino acid, in the growth media, e.g., a gene coding for a protein critical to the metabolic pathway leading to a specific amino acid;

Viruses, for example, viruses that invade human cells, e.g., human immunodeficiency virus (HIV) or herpes simplex; viruses that invade bacteria, e.g., bacteriophage; and Proteinaceous agents that cause disease, for example, proteins that are associated with disease in human cells, e.g., proteins that are associated with neurological disease, e.g., Jacob Creutzfeld disease, e.g. prions.

In a preferred embodiment, the substance is a particle, e.g., an insoluble particle, e.g., a polymeric particle. The particle can be a magnetically responsive particle. Molecules, e.g., nucleic acid molecules can be associated, e.g., adhered to or coupled to the particle.

In a preferred embodiment the gel is caused to contract by exposing it to environmental stimuli; this stimuli can include changes in temperature, ionic composition, pH, light, electric field, the presence of specific molecules, stress and solvent composition.

In a preferred embodiment the gel is chosen from the group of N-alkylacrylamides polymers, e.g., N-isopropylacrylamide (NIPA) and N,N-Diethylacrylamide (DEAAm).

Steps 2 and 3 can be repeated, e.g., to provide further concentration of the substance within the gel. They can be repeated at least 2, 10, 50, 100, 250, or 500 times. Thus, in a preferred embodiment the method further includes:

causing the gel of step 3 to expand, e.g., by exposing it to, e.g., temperature, and contacting the gel while in the expanded state, with a substance, e.g., a solute in a solution, and allowing the substance to enter the gel; causing the expanded intelligent gel to contract, wherein upon contraction molecules of the substance remain in the gel. The substance can be the same substance as in step 3 (allowing a further concentration of the substance) or can be a different substance.

In a preferred embodiment a plurality of substances to be disposed inside the gel are brought into contact with the gel, simultaneously, sequentially, or both simultaneously and sequentially.

In a preferred embodiment, a step of the method is performed in response to a signal generated by a computer.

In general, the invention features, a method for preparing an array of gel pads. The method includes:

providing a first gel layer, e.g., an intelligent gel, on a substrate;

selectively removing portions of the first gel layer to create voids in the first gel layer, providing a second gel in the voids; and removing the first gel layer, such that an array of gel pads is provided.

In a preferred embodiment, a step of the method is performed in response to a signal generated by a computer.

In another aspect, the invention features, a method of making a pattern in a gel layer on a substrate, e.g., forming a mold, or forming an array of gel pads. The method includes:

(1) forming, e.g., by casting, a layer of a gel, e.g., an intelligent gel on a substrate, e.g., on a non-porous substrate, e.g., a glass or silicon plate, or a porous substrate, e.g., a membrane or a glass or a silicon support with microchannels, e.g., with channels less than 10 micrometers in diameter, (2) exposing a region of the gel layer to treatment which causes the gel to liquefy. E.g., a laser rasters over the gel layer and irradiates selected gel portions in the configuration of an array (see also Patent Cooperation Treaty Publication WO95/04834). Selective exposure can also be achieved, e.g. by protecting an area of the gel layer, e.g., such that the unprotected area defines an array configuration on the substrate (e.g., a 100×100 array of gel pads). An area of the gel can be protected by masking the gel layer, e.g., with a mask such as is conventionally used in photolithography, the mask protects the masked gel from a phase change; and (3) removing the treated or untreated area of the gel, e.g., removing the area of the gel layer which has been exposed to the treatment, thereby defining a pattern of gel on the substrate. By way of example, gel in an area which are exposed to treatment, e.g., the laser source, also become liquefied and the liquefied portions are removed, e.g., by gentle washing. (The gel layer can also be selectively heated by other means, such as an array of heated wires or probes which are brought near to, or into contact with, the surface of the gel layer.)

The method can be used to produce a gel layer having a pattern, e.g., an array of voids, e.g., channels, grooves, holes, or wells, or the like, formed by removal of the gel portion exposed to the treatment, e.g., a laser source.

In a preferred embodiment the method includes exposing the unprotected area of the gel to treatment which causes liquidation and removing gel exposed to the treatment, to thereby form a pattern of gel on the substrate. By way of example, the exposed portions of the gel liquefy and are poured off or washed off with a suitable solvent, without disturbing the remaining gel.

In a preferred embodiment, a gel which liquefies in response to UV irradiation is cast is in a thin film on a substrate such as a glass plate. The masked gel layer is exposed to ultraviolet light. The exposed portions of the gel liquefy and are poured off or washed off with a suitable solvent, without disturbing the array. After irradiation and removal of the mask, a pattern, e.g., an array of gel pads is obtained. Alternatively, conventional gels can be used.

The gel can incorporate reagents, such as polynucleotide probes for capturing fragments of DNA from a solution; alternatively, such reagents can be added after the array has been formed.

In preferred embodiments the method produces an array of voids and the method further includes filling one or more void with a gel, e.g., a different gel than the original gel. A void or voids can be filled with, e.g., a second gel which is, e.g., a different intelligent gel or a conventional gel, such as polyacrylamide. The second gel can be allowed to solidify, to form a composite gel layer, one having an area formed by the first gel and an area formed by the second gel. By way of example, the method can be used to form an array of conventional gel pads within a framework of an intelligent gel layer. The method can be used to form an array of intelligent gel pads within a framework of a conventional gel layer. The method can also be used to form an array of intelligent gel pads within a framework of an intelligent gel layer. The composite gel layer can be exposed to a treatment which causes a phase change to remove one of the gel components. By way of example, the composite layer is then heated (e.g., by placing the substrate in a warming bath or a warming oven) to liquefy the intelligent gel layer, which is then removed by washing or pouring off the liquefied material. An array of gel pads remains on the substrate and can be further processed, if desired.

In a preferred embodiment, a step of the method is performed in response to a signal generated by a computer.

In another aspect, the invention features, a device which includes an intelligent gel which changes volume or size in response to an analyte and a device, e.g., a piezo device, for evaluating a change in the volume or size of the intelligent gel.

In a preferred embodiment the intelligent gel swells in response to a change, such as the presence of an analyte of interest. For example, an intelligent gel which swells in response to pH changes in provide in a gel pad on a support.

In a preferred embodiment the intelligent gel includes, an enzyme, e.g., glucose oxidase, and the reaction of the enzyme with its substrate, e.g., glucose oxidase with glucose, changes the pH of the gel. Thus, in the presence of the analyte, e.g., glucose, in a sample solution which is brought into contact with the gel pad, the gel pad will shrink. A gel pad can be provided adjacent to a piezocrystal, such that changes in gel pad swelling produce a piezoelectric signal, which can be detected and correlated with the glucose concentration.

In another aspect, the invention provides, a method of forming a gel, e.g., an array of gel pads, on a substrate. The gel can be an intelligent gel, e.g., an intelligent gel described herein. The method includes:

(1) providing a first substrate having disposed thereon a gel layer, e.g., a patterned layer of gel, e.g., an array of gel pads, or a pattern of gel which defines one or an array of voids;

(2) providing a second substrate;

(3) transferring the gel layer from the first substrate to the second substrate, e.g., transferring one or more, e.g., an array of gel pads, on the first substrate to in array of gel pads on the second substrate.

In a preferred embodiment, the gel layer, e.g., a pattern of gel, on the first substrate is formed by a method described herein.

In a preferred embodiment: the gel is not covalently attached to the first substrate; the gel is not covalently attached to the second substrate; the gel is not covalently attached to the first or second substrate; the gel is covalently attached to the first substrate but not to the second; the gel is covalently attached to the second substrate but not to the first.

In a preferred embodiment the gel on the first substrate is inspected to determine if it possesses a quality, e.g., a defect, before transfer to the second substrate. By way of example, the quality of a gel pad can be evaluated. Undesirable gel pads (e.g., a pad of the wrong shape or size) can be removed before the final array is prepared on the second substrate. This step can be controlled by a computer. This procedure can prevent the formation of arrays which contain faulty or non-standard gel pads.

In a preferred embodiment the gel on the first substrate is contacted with a reagent prior to transfer to the second substrate. By way of example, the gel pads can be further processed (e.g., washed, imparted with an additional component, such as a protein, nucleic acid, label, buffer, or the like) prior to transfer of the gel pads from the first substrate to the array format on the second substrate.

In a preferred embodiment the first and second substrates are the same material.

In a preferred embodiment the first and second substrates differ, e.g., in size, flexibility, transparency, composition, hydrophilicy, hydrophobicity, ability to adhere to a gel layer, or state of derivitization, with e.g., a functional group. For example, gel pads can be prepared on a first substrate, e.g., a flexible substrate such as a tape, and then transferred to a second substrate, e.g., a less flexible substrate such as a glass or plastic plate, in an array format, to provide a gel pad array on the second substrate.

In a preferred embodiment the gel layer is transferred by bringing the first substrate into sufficiently close proximity to the second such that the gel is transferred from the first to the second, e.g., by contacting the second substrate with the gel on the first substrate, such that the gel is transferred from the first substrate to the second substrate. The transfer can be facilitated by using first and second substrates which have different surfaces, e.g., a hydrophobic first substrate and a hydrophilic second substrate; in this example, a hydrophilic gel pad will be more adherent to the second substrate and will be transferred from the first substrate to the second substrate when the two substrates are pressed together. The transfer can be facilitated in other ways. For example, the gel pad can be electrically charged, and the electric charge of the first and/or second substrate can be adjusted such that the gel pad is repelled from the first substrate and attracted to the second substrate.

In a preferred embodiment, a layer of an intelligent gel is disposed between the substrate and the gel layer. A phase change can be induced in the intelligent gel, e.g., to promote transfer of the gel layer form the first substrate to the second substrate. For example, the first substrate can be coated with a thin layer of an intelligent gel such as described above, prior to the deposition of the gel pads on the first substrate. When the first and second substrates are placed into close contact, the intelligent gel can be liquefied or otherwise modified to promote the release of the gel. For example, for an intelligent gel, such as "Smart Hydrogel", which liquefies at cooler temperatures, liquefaction can be accomplished by cooling the first and/or second substrate. When the intelligent gel is liquefied, the gel pads disposed on the intelligent gel layer on the first substrate cannot adhere to the first substrate, and are transferred to the second substrate. Similarly, for other intelligent gels, the first and/or second substrates (or selected portions thereof) can be heated, subjected to an electric current, contacted with a solution having a high pH or salt concentration, and the like, to liquefy or soften the intelligent and thereby release the gel pads from the first substrate.

In a preferred embodiment, a gel, e.g., one or more gel pads, is transferred from a first substrate to the second substrate, and a second gel, or second gel pad or second array of gel pads is transferred from a third substrate to the first substrate. Gel pads can be transferred to the second substrate in groups, e.g., in a row or rows, or one at a time. Thus, a plurality of first substrates can be used to transfer elements of a pattern to a substrate.

In a preferred embodiment, substance which promotes adhesion of the gel to the second substrate is delivered, e.g., by a piezo dispenser, to a gel pad prior to transferring it to the second substrate. The substance can activate sites which allow the gel to bind to the second substrate. Alternatively, substance which promotes adhesion of the gel to the second substrate is delivered, e.g., by a piezo dispenser, to the second substrate prior to transferring the pad to the second substrate.

In a preferred embodiment, a step of the method is performed in response to a signal generated by a computer.

The invention also features multi-layered gel pad constructs and methods of making and using them.

Accordingly, in one aspect, the invention provides a gel, e.g., a gel pad, which includes at least two gel layers, preferably in contact with each other, e.g., a first gel layer on which is disposed a second gel layer, or first gel layer adjacent to and in contact with a second gel layer. A multi-layer gel of the invention can have two, three, four, or more layers. In a preferred embodiment at least one of the first gel layer and the second gel layer includes an intelligent gel.

In a preferred embodiment a first gel layer includes a first reagent, e.g., any of a polynucleotide (e.g., a probe suitable for performing sequencing by hybridization), a nucleic acid, e.g., DNA, RNA, or a probe; a protein, e.g., an enzyme which modifies DNA; a particle; a cell; or a reactant; and a second gel pad layer includes a second reagent, e.g., any of a polynucleotide (e.g., a probe suitable for performing sequencing by hybridization), a nucleic acid, e.g., DNA, RNA, or a probe; a protein, e.g., an enzyme which modifies DNA; a particle; a cell; or a reactant.

In a preferred embodiment the gel layers have different porosities. For example, the first layer has a larger porosity than does the second, e.g., the first layer allows free passage of a substance, e.g., molecule, e.g., a nucleic acid molecule, or cell, but the second layer has a porosity which, when compared with the first, does not allow free passage of the substance. Such a second gel layer can be disposed over and covering the first gel layer; the second gel layer can be a gel having an effective pore size small enough to prevent the diffusion of high-molecular-weight substances, such as nucleic acids or proteins. The second layer thus serves as an effective barrier to prevent diffusion of substances, e.g., proteins, from a sample solution into the first gel layer, or from the first gel layer into solution. The multi-layer gel pad can prevent interference from sample constituents, or can prevent the loss of valuable components from the first gel layer.

In another embodiment a layered gel has a first layer having a first ionic strength and a second layer having a second ionic strength, e.g., a first gel layer has a, relatively, low ionic strength, e.g., an ionic strength lower than the ionic strength of a sample solution to be applied to the gel pad array, and the second layer has a, relative to the first layer or a solution to be applied, a high ionic strength. The second, protective or filtering gel layer can cover or encapsulate the first gel pad layer. The difference in ionic strength can promote transfer of a component into or out of the layers. E.g., the low ionic strength of the first gel layer can promote osmotic movement of sample components into the first gel layer, e.g., increasing the sensitivity of the first gel layer for a sample component of interest.

In another aspect, the invention features, a gel described herein, wherein a cell, e.g., a living cell, is disposed with in the gel. Such gels are sometimes referred to herein as "cell pads".

In a preferred embodiment, the gel is a multi-layered gel described herein, having a first layer without cells, and second layer which includes cells (e.g., bacterial or eukaryotic cells). (Alternatively, cells can be grown on top of a gel layer, without being immobilized within a second gel layer).

In preferred embodiments: a first gel layer not having a cell is disposed adjacent a second, cell-containing gel layer; a cell is immobilized in a second gel layer which encapsulates a first gel layer.

In a preferred embodiment a cell is disposed on the surface of a gel layer.

In preferred embodiments a first gel layer includes detection means for detecting the presence (or absence) of a cell constituent (such as DNA) or a product of cellular metabolism (such as proteins, or products of transcription). The cell can be provided in the second layer or on the surface of the first or second layer.

In another aspect, the invention features, a method of detecting analyte, e.g., cell constituent (such as DNA) or a product of cellular metabolism (such as proteins, or products of transcription). The method includes:

(1) providing a gel having a first layer which includes a molecule for detecting the analyte and a second layer having a cell, which, e.g. releases, produces, inactivates, modifies, or otherwise affects the level of the analyte;

(2) detecting the analyte.

In a preferred embodiment, the first, the second, or both layers is an intelligent gel, e.g., an intelligent gel described herein.

In a preferred embodiment a biological molecule is attached to the first layer, e.g., a protein or nucleic acid; the biological molecule interacts with a second molecule, e.g., a biological molecule, e.g., a protein that forms a multimeric complex with the immobilized protein, e.g., a protein dimer; or a complex between the immobilized protein and a nucleic acid molecule, e.g., single or double stranded DNA, e.g., the nucleic acid binding site for a transcription factor, replication factor, structural protein, e.g., a matrix attachment protein or a histone; the attached biological molecule interacts with a small molecule, e.g., a drug candidate; the protein attached to the gel contains a tag, e.g., a nucleic acid tag, that can be used to identify the protein, e.g., by the process of polymerase chain reaction (PCR), or by binding to a molecule that emits a strong signal, e.g., a fluorescent signal.

In a preferred embodiment a cell in one layer can secrete or release molecules, such as growth factors, which can be monitored, e.g., by the use of capture molecules in another layer of the multi-layer gel pad.

In a preferred embodiment the cell is lysed and cellular components measured.

In a preferred embodiment the method evaluates the response of a cell to a stimulus, such as addition of a growth factor, a toxin, a drug, or the like.

In a preferred embodiment the gel is configured to permit cells in one layer (or pad) to secrete, release, or otherwise modulate the level of a molecule which influences the growth of other cells a second layer or pad, e.g., in an adjacent pads. Thus, complex cell-based assays, e.g., autocrine system assays, or developmental assays, can be reduced to microscale format. The cells in the first and second component can be the same or different.

In a preferred embodiment, a step of the method is performed in response to a signal generated by a computer.

In another aspect, the invention features, a method of detecting an analyte, e.g., cell constituent (such as DNA) or a product of cellular metabolism (such as proteins, or products of transcription). The method includes:

(1) providing a gel having a first layer which includes a molecule for detecting the analyte and a second layer having a cell, which, e.g., retains, releases, produces, inactivates, modifies, or otherwise affects the level of the analyte;

(2) detecting the analyte.

In preferred embodiments the molecule for detecting is an antibody or a functional variant of an antibody, e.g., an aptamer. The antibody is either expose to the second layer or an analyte released from the second layer. Preferably, the analyte contains an antigen recognized by the antibody. Alternatively, the analyte acts an antigen to antibodies that are either in solution or are present on the second layer.

In a preferred embodiment a population of molecules are attached to the first layer. For example, the first layer represents and array of gel pads, e.g., intelligent gel pads, that each are individually addressable and contain a unique population of attached molecules. The population of molecules in each gel pad can be either homogenous (i.e. all the same molecule), or under certain embodiments a heterogenous population of molecules (i.e. many different molecules). The molecules can be derived from cells, e.g., protein or nucleic acid, or derived from chemical synthesis, e.g., hormones or small molecules. The chemical synthesis process may represent many combinations of molecules, e.g., a combinatorial library of chemicals. In preferred embodiments, the gel pads containing molecules described herein can be exposed to phage that display a unique protein on the solvent exposed surface of the phage, e.g., phage used in the technique called phage display. In preferred embodiments, the phage is present in a population, where the phage, each expressing a unique protein, as a group provides many unique proteins on their solvent exposed surfaces. In preferred embodiments the phage population interacts with the molecules immobilized in the gel pads. In preferred embodiments, the gel pads are intelligent and are present in the expanded state. In preferred embodiments unbound phage are removed from the first layer and any surrounding chamber. In preferred embodiments a population of cells are presented to the first layer with a gel pad array that contains molecules associated with a select group of phage.

The invention also provides gel pad arrays on a flexible support, such as a flexible tape, and methods for making and using them, and carriers for storing gel pad arrays on tapes. The gel can be an intelligent gel, e.g., an intelligent gel described herein. The arrays can be used for sequencing by hybridization (e.g., where the pads include nucleic acid strands immobilized within the gel matrix), for cell based assays (e.g., where the pads include, or are adjacent to and contacting, living cells), and for other uses which will be apparent to one of ordinary skill in the art.

In one aspect, the invention provides flexible tape having a gel pad array disposed on a surface of the tape. In preferred embodiments: the tape comprises means for preventing compression of gel pads when the tape is wound on a reel more preferably, the means includes at least one ridge which extends along a length of the tape.

In another aspect, the invention provides a carrier for a tape having gel pad arrays thereon. The carrier includes a housing, at least one tape reel for winding the tape, and visible or machine-readable indicia for storing information about the tape stored in the carrier.

In one aspect, the invention provides gel pad arrays on flexible substrates, such as tapes. A variety of tapes can be employed as substrates for the gel pad arrays. Preferred tapes are biocompatible and/or compatible with test conditions, e.g., as are used for performing assays (to avoid interference with such assays). In addition, preferred tapes are relatively resistant to stretching, to reduce distortion of gel pad arrays deposited on the tape, e.g., during manufacture or storage of the tape. One preferred material for a tape substrate is polystyrene tape, which is commercially available from several suppliers.

A tape substrate can be transparent or translucent, and optionally includes a magnetic coating for information storage. The film can optionally be optically encoded.

If a tape having gel pad arrays disposed on a tape surface is wound up, gel material could potentially be transferred from one tape surface (e.g., the top surface) to another tape surface (e.g., the tape back) which is pressed against the first surface when the tape is wound. To prevent such transfer and consequent loss of gel pad integrity, the tape can be shaped or formed to have ridges or other structure along the length of the tape web. For example, as shown at the top of FIG. 1, a tape can be provided with ridges along each edge, running along the length of the tape, to prevent contact between a gel pad and the layer of tape which is wound above the pad. This configuration ensures that the integrity of the gel pad will not be disturbed during storage of the tape.

The invention also provides a carrier for tapes which includes gel pad arrays. The carrier includes a housing, and at least one tape reel (more preferably two reels) for winding the tape. As shown in FIG. 5, the tape carrier can resemble a conventional videotape housing, although the dimensions will vary depending upon factors such as the width, thickness, and length of the tape employed. In preferred embodiments, the housing includes a cover for closing the carrier, to thereby exclude light, moisture, dust, or other contaminants which could degrade the tape or the gel pads disposed thereon. The housing can optionally include visible or machine-readable indicia, such as a bar code or magnetic recording stripe, for storing information (such as date of manufacture, type of gel pad array, and the like) about the tape stored within the enclosure.

In general, the invention features, a method of analyzing, e.g., sequencing all or a part, e.g., a single nucleotide of, a polynucleotide sequence in a sample. The method includes:

providing a sample which includes a polynucleotide sequence to be analyzed;

providing an array of a plurality of capture probes, wherein each of the capture probes is positionally distinguishable from other capture probes of the plurality on the array, and wherein each positionally distinguishable capture probe includes a unique (i.e., not repeated in another capture probe) region complementary to the plurality of selector probes and wherein the array is a gel pad array described herein (each of the plurality of probes can be in its own gel pad);

hybridizing the selected nucleic acid molecule with the array of capture probes, thereby detecting or identifying a selected nucleic acid molecule which bound to the polynucleotide sequence and thereby analyzing the polynucleotide sequence.

In preferred embodiments the method includes one or more enzyme mediated reactions in which a nucleic acid used in the method, a capture probe, a sequence to be analyzed, and or a molecule which hybridizes thereto, is the substrate or template for the enzyme mediated reaction. The enzyme mediated reaction can be: an extension reaction, e.g., a reaction catalyzed by a polymerase, e.g., for DNA amplification (e.g. Polymerase Chain Reaction (PCR)) or a base extension in the presence of labeled dideoxy nucleotides (e.g. Genetic Bit Analysis); a linking reaction, e.g., a ligation, e.g., a reaction catalyzed by a ligase (e.g., a ligation Chain Reaction (LCR) for DNA amplification); or a nucleic acid cleavage reaction, e.g., a cleavage catalyzed by a restriction enzyme, e.g., a Type IIs enzyme, or a cleavage reaction catalyzed by a ribozyme. The nucleic acid which hybridizes with the capture probe can be the substrate in an enzyme mediated reaction, e.g., it can be ligated to a strand of the capture probe or it can be extended along a strand of the capture probe. Alternatively, the capture probe can be extended along the hybridized selected nucleic acid. (Any of the extension reactors discussed herein can be performed with labeled, or chain terminating, subunits.) These reactions can be used to increase specificity of the method or to otherwise aid in detection, e.g., by providing a signal.

In preferred embodiments, the capture probe bound to a target becomes the substrate for an isothermal amplification reaction. In certain embodiments the target is an RNA molecule and the probe is a nucleic acid primer in a process known as Nucleic Acid Sequence-Based Amplification (NASBA), where a primer (Primer 1) attached to the RNA target is extended with a reverse transcriptase to form a cDNA copy of the RNA target, RNase degrades the RNA portion of the DNA:RNA hybrid to form single-stranded DNA, a second primer (Primer 2) anneals to the DNA and is extended by reverse transcriptase, T7 RNA polymerase recognizes the double-stranded DNA target and produces many copies of complementary RNA, and the process is repeated on these new molecules of RNA. In other embodiments, the capture probe bound to a target is used to prime a single-stranded, circular DNA molecule in a process known as Rolling Circle Amplification (RCA), e.g., a primer can be attached to a protein molecule that binds to a capture probe attached to the gel pad. In certain embodiments an endonuclease is used to nick the unmodified strand of a hemiphosphorothioate formed at its recognition site, thereby creating a site for nick translation by a DNA polymerase that generates a new target, a process that is known in the art as a Strand Displacement Assay (SDA).

In preferred embodiments the polynucleotide sequence is: a DNA molecule: all or part of a known gene; wild type DNA; mutant DNA; a genomic fragment, particularly a human genomic fragment; a cDNA, particularly a human cDNA.

In preferred embodiments the polynucleotide sequence is: an RNA molecule: nucleic acids derived from RNA transcripts; wild type RNA; mutant RNA, particularly a human RNA.

In preferred embodiments the polynucleotide sequence is: a human sequence; a non-human sequence, e.g., a mouse, rat, pig, primate.

In preferred embodiments the selector probes are coupled to a support prior to hybridizing with the target.

In preferred embodiments the selector or capture probes are coupled to a light transmissable support, e.g., an optical fiber or fiber optic rod. The fiber optic rod may contain a single selector or capture probe or an array of such probes. In preferred embodiments the selector or capture probes are attached to a gel, e.g., an intelligent gel. The In preferred embodiments the method is performed: on a sample from a human subject; and a sample from a prenatal subject; as part of genetic counseling; to determine if the individual from which the target nucleic acid is taken should receive a drug or other treatment; to diagnose an individual for a disorder or for predisposition to a disorder; to stage a disease or disorder.

In preferred embodiments the capture probes are single stranded probes in an array.

In preferred embodiments the capture probes have a structure comprising a double stranded portion and a single stranded portion in an array.

In preferred embodiments, the capture probe forms a double stranded region with the target that contains a DNA base pair mismatch, e.g., a bubble in the double stranded DNA or an intrastrand secondary structure, that is the subtrate for an enzymatic reaction, e.g., an enzymatic reaction mediated by resolvase or mutS or cleavase I, with the product of the first enzymatic reaction acting as the substrate for a second enzymatic reaction, e.g., a reaction with DNA polymerase in the presence of a nucleotide termoinator, e.g., a dideoxy nucleotide labeled with a fluorescent dye. Diagnostic assays incorporating some or all of these steps are known in the trade as enzymatic Mutation Detection (EMD) or Cleavase Fragment Length Polymorphism (CFLP).

In preferred embodiments hybridization is detected by mass spectrophotometry, e.g., by MALDI-TOF mass spectrophotometry.

In preferred embodiments hybridization is detected by a signal amplification molecule, e.g., hyperbranch chain DNA (bDNA); e.g. bDNA that binds to a probe linked to an enzyme that generates a calorimetric, fluorescent or proximity detection assay, e.g., probes linked to alkaline phosphatase. In certain embodiments the target to be amplified first binds to a branched DNA molecule called a capture extender that binds, in turn, to the bDNA which, in turn, binds to alkaline phoshatase probes. In other embodiments, the probe is a fluorescently labeled DNA molecule that is known to those skilled in the art as a molecular beacon.

In a preferred embodiment, a step of the method is performed in response to a signal generated by a computer.

In another aspect, the invention features, a method of performing a reaction. The method includes providing a first reactant, e.g., a protein, e.g., an enzyme, disposed within a first intelligent gel which changes porosity in response to an environmental parameter having a first value, e.g, a first temperature, ionic strength, or pH;

providing a second reactant, e.g., a protein, e.g., an enzyme, disposed within a second intelligent gel which changes porosity in response to an environmental parameter having a second value, e.g, a second temperature, ionic strength, or pH;

exposing the intelligent gels to the parameter at a first value, thereby causing a change in porosity of the first gel (and preferably not the second gel), and thereby modulating exposure of the first reactant to a target, e.g., a molecule or a cell or other biological structure;

exposing the intelligent gels to the parameter at a second value, thereby causing a change in porosity of the second gel (and preferably not the first gel), and thereby modulating exposure of the second reactant to a target, thereby performing a reaction.

In a preferred embodiment, the first exposure and the second exposure are performed: sequentially or simultaneously.

In a preferred embodiment, the first exposure and or the second exposure is repeated.

Targets can be disposed in intelligent gels and their release controlled analagously to reactant release, thus in a preferred embodiment a first target is disposed in a first target intelligent gel. In a preferred a second target is disposed in a second target intelligent gel.

In a preferred embodiment a target gel and a reactant gel (a target-reactant pair) are disposed such that upon modulation of a parameter which causes one or more of the gels to change volume, the target gel and reactant gel are brought into or out of proximity or contact, thus modulating the ability of target and reactant to come into contact. In preferred embodiments a plurality of such target-reactant pairs are provided. They can be individually activated by choosing intellingent gels which respond at different parameter values, e.g., different temperatures.

Members of a target-reactant pair can be on the same surface or on different surfaces. When on two different surfaces the surfaces can be manipulated to bring the pair closer or more distant to one another.

A target-reactant pair can be physically separated, such that molecules released form it do not interact with other target-reactant pairs.

Other embodiments are within the clams and the following description.

DETAILED DESCRIPTION

BRIEF DESCRIPTION OF THE DRAWINGS

FIG. 1 depicts gel pads of the invention which include living cells.

FIG. 2 also depicts gel pads 26 on a tape 21.

Figure 2:
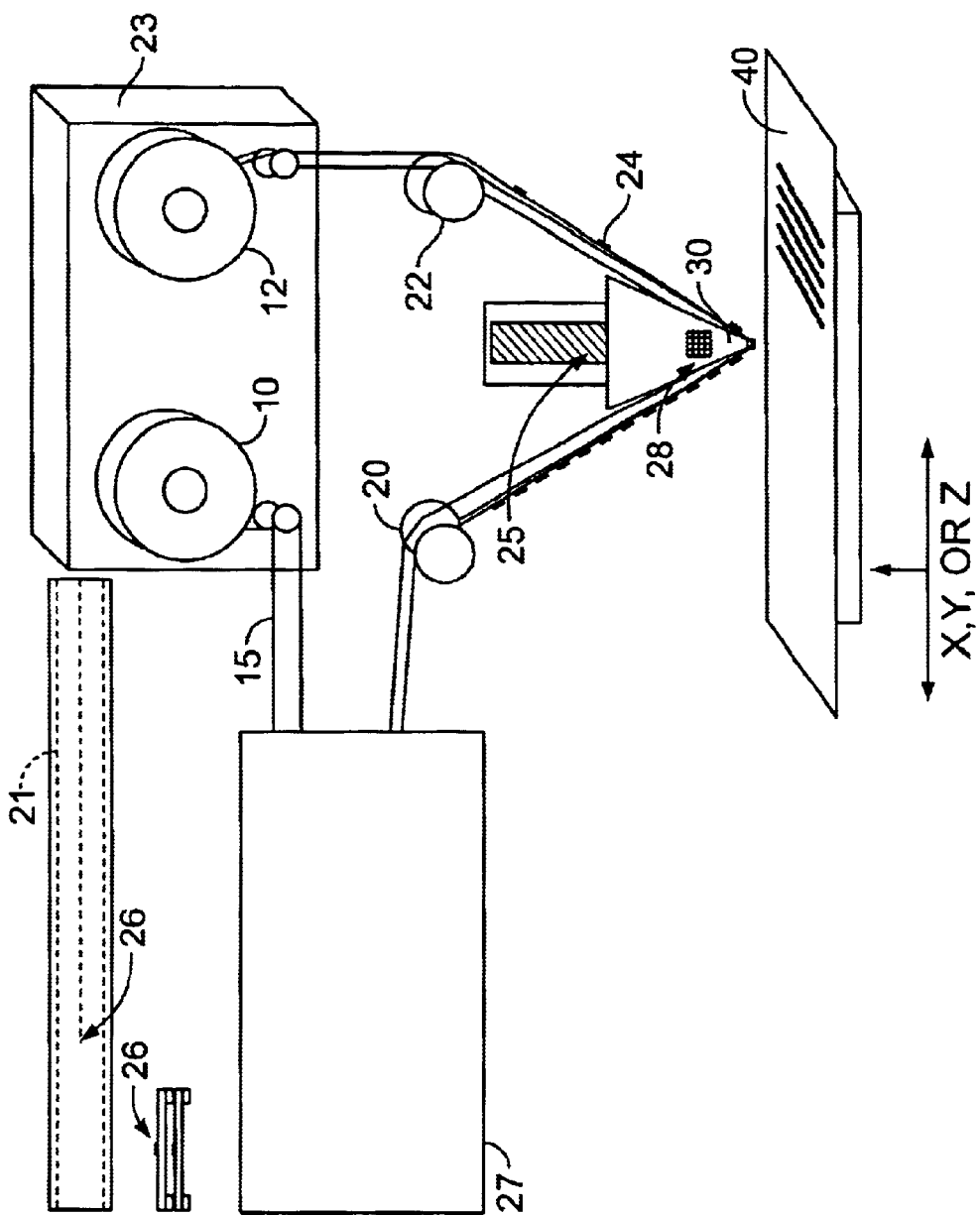
FIG. 2 depicts apparatus for preparing gel pads and transferring the pads to a substrate to form an array of gel pads.

This invention provides gel pads and gel pad arrays having a variety of uses, some of which are known in the art. The invention also provides methods for making the gel pads and gel pad arrays of the invention.

Gel Pads and Gel Arrays

The term "gel pad" as used herein refers to a discrete portion of a gel disposed on a substrate, such as a solid support, e.g., a plastic, glass, or metal substrate. The substrate can be any support suitable for supporting a gel pad, and can be rigid (e.g., a glass or plastic plate or sheet) or flexible (e.g., a tape), transparent (e.g., for performing optical measurements through the pad and substrate) or opaque. The properties of the support can be readily selected for use in any particular application. In preferred embodiments, the solid support is substantially non-reactive under conditions used to perform an assay or test procedure with the gel pad or gel pad array. An "array" can be any pattern of spaced-apart gel pads disposed on a substrate; arrays can be conveniently provided in a grid pattern, but other patterns can also be used. In preferred embodiments, a gel pad array according to the invention includes at least about 10 gel pads, more preferably at least about 50, 100, 500, 1000, 5000, or 10000 gel pads. In certain embodiments, the array is an array of gel pads of substantially equal size, thickness, density, and the like, e.g., to ensure that each gel pad behaves consistently when contacted with a test mixture. In certain embodiments, however, the pads of a gel pad array can differ from one another; e.g., a mixed gel pad array can be constructed which includes more than one size or type of gel pad, e.g., gel pads made of different gel materials, or which entrap different species such as reagents or polynucleotide probes. In certain preferred embodiments, gel pads in an array are less than about 1 mm in diameter (or along a side, e.g., in the case of square gel pads), more preferably less than about 500 microns, still more preferably less than about 100, 75, 50, 25, 10, 5, 1, or 0.1 micron in diameter.

A gel pad can have any convenient dimension for use in a particular assay. In preferred embodiments, a gel pad is thin enough, and porous enough, to permit rapid diffusion of at least certain reaction components into the gel pad when a solution or suspension is place din contact with the gel pad. For example, in one embodiment, a gel pad array for use in sequencing by hybridization permits polynucleotide fragments from a sample mixture to diffuse (within a conveniently short time period) into the gel pads and hybridize to oligonucleotide capture sequences disposed within the gel pads. In certain preferred embodiments, a gel pad (e.g., in an array of gel pads) has a thickness of at least about 0.1, 1, 5, 10, 20, 30, 40, 50 or 100 microns. In certain preferred embodiments, a gel pad (e.g., in an array of gel pads) has a thickness of less than about 1 millimeter, 500 microns, 200, 100, 50, 40, 30, 20, 10, 5, 1 or 0.1 microns.

It will be appreciated from the foregoing that a gel pad can entrap additional chemical species, if desired, e.g., to perform assays with or within the gel pad. For example, gels which include DNA probes have been used for SBH (for example, U.S. Pat. No. 5,552,270 to Khrapko et al. and U.S. Pat. No. 5,525,464 to Drmanac et al.). Thus, a gel pad can be prepared such that a chemical species is trapped within the gel pad, or a desired species can be added after the gel pad has been prepared, e.g., by contacting a preformed gel pad with a solution of the reagent and allowing the reagent to diffuse into the gel pad. Examples of reagents which can be entrapped, suspended or dissolved in a gel pad include proteins, such as enzymes (e.g., ligases), which can be useful for positional SBH (see, e.g., Cantor, U.S. Pat. Nos. 5,503,980 and 5,631,134)), polynucleotides, growth factors (e.g., for use with cells, e.g., see infra), salts and the like.

Derivatized Gels

Gels described herein can be made with derivatized subunits, e.g., subunits with are coupled to a molecule of interest. A gel component, e.g., layer or pad (e.g., in an array) can be prepared through the use of a derivatized monomer unit, followed by formation of the gel component by polymerization of the monomer. For example, acrylic acid can be readily derivatized with a polynucleotide (e.g., a probe for use in SBH); for example, a polynucleotide can be coupled to acrylic acid through the use of a conventional coupling reagent such as dicyclohexylcarbodiimide (DCC)

(or a water-soluble derivative thereof such as 1-(3-dimethylaminopropyl)-3-ethylcarbodiimide, EDC). Alternatively, amino or aldehyde groups in the gel can couple to oligonucleotides bearing aldehyde or amino groups, respectively, in the presence of a reducing agent, e.g., as described in Timofev et al., 1996, *Nucleic Acids Research*, 24:3142–3148. A spacer or linker moiety can be used to increase the distance between the acrylate monomer and the polynucleotide, if desired, e.g., to increase mobility of the polynucleotide in the polymer). The resulting acrylic ester of the polynucleotide can then be disposed in an array format on a substrate, e.g., by dispensing a solution of the acrylic ester through a nozzle or array of nozzles (such as conventional piezoelectric ink-jet printing nozzles; see also Patent Cooperation treaty Publication WO95/04594). Alternatively, an array format can be provided by using a cast or mold. The array of droplets, e.g., dispensing to a mold containing an array of voids, is then polymerized in situ to provide an array of gel pads which incorporate a polynucleotide covalently bound to the gel polymer.

Gel Arrays Using Intelligent Gels

In one aspect, the invention provides methods for making gel pads and gel pad arrays. In certain preferred embodiments, gel pads and gel pad arrays can be conveniently prepared by use of "intelligent gels."

An intelligent gel, as used herein, can be a gel having an internal lattice which defines pores in the gel structure. In preferred embodiments the lattice is covalently stabilized. An intelligent gel can exist in two states: a first state in which pore size is, relative to that of the second state, small, and a second state in which the pore size is, relative to the first state, large. Although the pore size changes between states, the lattice maintains its integrity and the porephase change is generally reversible. Intelligent gels can fall into one of two major classes, "Expandable intelligent gels," see, Li and Tanaka 1990, *J. Chem Phys*, 92:1365; Matsuo and Tanaka, 1988,*J. Chem Phys*, 89:1695–1703; Matsuo and Tanaka, 1992, *Nature*, 358:482; Kokutata et al., 1991, *Nature*, 351:302; and Annaka and Tanaka, 1992,*Nature*, 335:430, in which pore seize change is accompanied by a change in the volume of the gel, and "lattice constant" intelligent gels in which pore size change is accompanied by a change in internal condensation, see Tokita and Tanaka, 1991, *Science*, 253:1121–1123. See, also e.g., Kajiwara et al., "Synthetic Gels on the Move", *Nature*, vol. 355, pp. 208–209 (1992); Kwon et al., "Electrically Erodible Polymer Gel for Controlled Release of Drugs", Nature, vol. 354, pp. 291–293 (1991); Suzuki et al., "Phase Transition in Polymer Gels Induced by Visible Light", *Nature*, vol. 346, pp. 345–347 (1990); Osada et al., "Intelligent Gels", *Scientific American*, pp. 82–87 (1993); R. Dagani, "Intelligent Gels," *Chem. Eng. News.*, Jun. 9, 1997).

In a preferred embodiment, the intelligent gel has an expanded pore state and a minimized pore state. The expanded pore state will allow passage of a molecule which is up to 5, 10, 50, 100, 500 or 1,000 times the molecular weight of the largest molecule which is allowed passage by the minimized pore state. In a preferred embodiment the gel allows, e.g., when the pores are expanded, passage of molecules (or particles) of at least 0.1, 0.5, 1, 5, 10, 50, 100, 200, 500, or 1,000 kilodilations to enter the gel.

Expandable intelligent gels undergo an isotropic swelling and shrinking process where the gel either expands or contracts equally in both length and width. The process of swelling and shrinking can be either continuous or discontinuous, based on the balance between molecular forces, e.g., electrostatic, osmotic, hydrophobic, Van der Waals, hydrogen bonding and ion—ion interactions. Examples of intelligent gels include gels which become softer or firmer (e.g., solidify or liquefy) in response to changes in temperature, salt concentration (e.g., ionic strength), pH, exposure to radiation (e.g., ultraviolet (UV) radiation), presence or absence of a selected metal ion, electrical current, magnetic field, and the like. For example, a copolymer of poly(acrylic acid) and poly(N-isopropylacrylamide) has been reported to be temperature-sensitive, swelling at lower temperatures and collapsing at higher temperatures (Tanaka et al., Faraday Discuss. 101:201 (1995)). One of ordinary skill in the art will be able to select an intelligent gel with the desired properties for a selected application using no more than routine experimentation. In certain preferred embodiments, an intelligent gel for use in the present invention is responsive (e.g., liquefies) in response to an increase in temperature or irradiation with ultraviolet light.

Examples of suitable intelligent gels include:

I. N-ackylacrylamide group, e.g., N-isopropylaerylamide and N,N-Diethylaerylamide.

II. Independent interpenetrating polymer networks (IPNs) in which one cross-linked network is intertwined with another, e.g., poly(acrylic acid) and poly(N,N-Dimethylacrylamide), or poly(ethylene oxide) and poly (N-Acryloylpyprolidine).

The IPNs are particularly suitable for pulsated gels pads (gel pads that exhibit rapid expansion/contraction cycles).

Gels can be liquefied at ambient temperature (25° C.) and solid at higher (i.e., body) temperatures (37° C.).

Other intelligent gels are described, e.g., in Bromberg and Ron, 1998, *Advanced Drug Delivery Reviews*, 31:197–221; Schild, 1992, *Prog. Polym. Sci.* 17:163–249; Irie, 1993, *Adv. Polym. Sci.* 110:49–65; Okano, 1993, *Adv. Polym. Sci.,* 110:179–200; Sen et al., 1998, *Polymer,* 40:913–917. Also useful are bilayer membrane gels, e.g., as described in Tsujii et al., 1997, *Macromolecules,* 30:7397–74029; and Hayakawa et al., 1997, *Langmuir,* 13:3595–3597; intelligent gels that can recognize and recover molecules, e.g., as described in Tanaka et al., 1996, *Faraday Discuss.,* 102–206; and Umeno et al., 1998, *Bioconjugate Chem,* 9:719–724; intelligent gels that can function as a detachable cell culture substrate, e.g., as described in von Reum et al., 1998,*J. Biomed Matter Res,* 40:631–639; Intelligent gels used for drug delivery that are comprised, e.g., of block co-polymers of poly(ethylene) oxide and poly(propylene) oxide, otherwise known in the trade as Pluronics or Poloxamers, e.g., as described in Alexandridis and Hatton, 1995, *Colloid Surfaces A,* 96:1–46; and Wang and Johnson, 1991, *J. Appl. Polym. Sci.,* 43: 283–292; intelligent gels attached to a fibor optic rod, e.g., as described in McCurley, 1994, *Biosensors & Bioelectronics,* 9: 527–533; polymerized colloidal crystal hydrogels used as chemical sensors, e.g., as described in Holtz and Asher, 1997, *Nature,* 389: 829–832; intelligent gels used to encapsulate proteins, e.g., as described in Serres et al., 1996, *Pharm Res,* 13:196–201; and Baudys et al., 1996, *Drug Delivery Systems*, Springer, Tokyo, pp 112–115.

In an illustrative embodiment, gel, e.g., an intelligent gel, can be used to prepare a gel pad array. The gel pads can comprise an intelligent gel, or the intelligent gel can be used as a form or mold to prepare a gel pad array. For example, in one embodiment, a gel which liquefies in response to UV irradiation is cast is in a thin film on a substrate such as a glass plate. The gel can incorporate reagents, such as polynucleotide probes for capturing fragments of DNA from a solution; alternatively, such reagents can be added after the array has been formed. The gel is allowed to cool and solidify. The gel layer is then masked, e.g., with a mask such as is conventionally used in photolithography; the mask protects gel portions in an array configuration on the substrate (e.g., a 100×100 array of gel pads). The masked gel layer is exposed to ultraviolet light. The exposed portions of the gel liquefy and are poured off or washed off with a suitable solvent, without disturbing the array. After irradiation and removal of the mask, an array of gel pads is obtained.

Examples of the use of photolithographic masks in the generation of arrays of gel, e.g., as described in Guschin et al., 1997, *Analytical Biochemistry*, 250:203–211.

Alternatively, a gel, e.g., an intelligent gel can be used as a mold or form for preparing a gel pad array. A gel which is temperature-responsive is cast on a substrate. The gel layer is then exposed to a laser, which is rasters over the gel layer and irradiates selected gel portions in the configuration of an array (see also Patent Cooperation Treaty Publication WO95/04834). The portions of the gel pad which are exposed to the laser source are heated and become liquefied; the liquefied portions are removed, e.g., by gentle washing. (The gel layer could be selectively heated by other means, such as an array of heated wires or probes which are brought near to, or into contact with, the surface of the gel layer.) The gel layer now has an array of "holes" formed by removal of the gel portions exposed to the laser source. These "holes" can be filled with a second gel (which can be a different intelligent gel or a conventional gel, such as polyacrylamide); the second gel is permitted to solidify, forming an array of gel pads within the intelligent gel layer. The slide is then heated (e.g., by placing the substrate in a warming bath or a warming oven) to liquefy the intelligent gel layer, which is then removed by washing or pouring off the liquefied material. An array of gel pads remains on the substrate and can be further processed, if desired.

It will be appreciated that the methods of using intelligent gels to prepare gel pad arrays will have many applications. The mild conditions employed can be tailored to the preparation of a wide variety of intelligent and conventional gel pad arrays, preferably without degradation of sensitive reagents, such as polynucleotide probes, which may be present in the gel layer. Methods for preparing gel pads, e.g., such as conventionally known or described herein, can be combined, if desired.

Furthermore, the use of intelligent gels in gel pad arrays provides additional advantages. For example, an intelligent gel pad can be provided which swells in response to a change, such as the presence of an analyte of interest. For example, an intelligent gel which swells in response to pH chances in provide in a gel pad on a support. The gel pad includes glucose oxidase. The reaction of glucose oxidase with glucose produces gluconic acid, lowering the pH of the gel. Thus, in the presence of glucose in a sample solution which is brought into contact with the gel pad, the gel pad will shrink. A gel pad can be provided adjacent to a piezocrystal, such that changes in gel pad swelling produce a piezoelectric signal, which can be detected and correlated with the glucose concentration.

Gel pad arrays can also be prepared by treating the surface of the substrate to create a pattern of alternating hydrophobic and hydrophilic sites on the surface. For example, a glass surface can be silated with a conventional silating reagent to prepare a patterned surface having hydrophobic and hydrophilic portions. A gel, such as an intelligent gel, is then poured onto the surface. A hydrophobic gel will be repelled by a hydrophilic surface, while a hydrophilic gel will be repelled by a hydrophobic surface. A patterned surface can be used to urge the liquefied gel into a pre-selected pattern on the substrate, thereby forming a gel pad array.

Another method for preparing a gel pad array comprises preparing individual gel pads, or sub-arrays of gel pads, on a first substrate, and then transferring the individual gel pads to a second substrate, in array format, to prepare a gel pad array on the second substrate. This method can be used to substantially avoid covalent attachment of the gel pad to the second substrate. In addition, the gel pads prepared on the first substrate can be examined to ensure quality of the individual gel pads, and faulty gel pads (e.g., of the wrong shape or size) can be removed before the final array is prepared on the second substrate. This procedure can prevent the formation of arrays which contain faulty or non-standard gel pads. Moreover, the gel pads can be further processed (e.g., washed, imparted with an additional component such as a protein, and the like) prior to transfer of the gel pads from the first substrate to the array format on the second substrate.

For example, gel pads can be prepared on a first substrate, such as a tape, and then transferred to a second substrate, such as a glass or plastic plate, in an array format, to provide a gel pad array on the second substrate. The gel pads can be transferred by contacting the first and second substrates, e.g., by pressing the first substrate against the second substrate, such that the gel pads are transferred from the first substrate to the second substrate. The transfer can be facilitated by making using first and second substrates which have different surfaces, e.g., a hydrophobic first substrate and a hydrophilic second substrate; in this example, a hydrophilic gel pad will be more adherent to the second substrate and will be transferred from the first substrate to the second substrate when the two substrates are pressed together. Alternatively, gel pads can be modified prior to the transfer process by a reagent, e.g., a reagent dispensed from a piezoelectric fluidic dispensing robot, said reagent creating a change in the gel pad in the tape, e.g., activating chemical groups present in the gel pad on the first substrate such that the gel pad binds to the second substrate.

The transfer can be facilitated in other ways. For example, the gel pad can be electrically charged, and the electric charge of the first and/or second substrate can be adjusted such that the gel pad is repelled from the first substrate and attracted to the second substrate. In another embodiment, an intelligent gel can be employed to facilitate the transfer. For example, the first substrate can be coated with a thin layer of an intelligent gel such as described above, prior to the deposition of the gel pads on the first substrate. When the first and second substrates are placed into close contact, the intelligent gel can be liquefied. For example, for an intelligent gel, such as "Smart Hydrogel", which liquefies at cooler temperatures, liquefaction can be accomplished by cooling the first and/or second substrate. When the intelligent gel is liquefied, the gel pads disposed on the intelligent gel layer on the first substrate cannot adhere to the first substrate, and are transferred to the second substrate. Similarly, for other intelligent gels, the first and/or second substrates (or selected portions thereof) can be heated, subjected to an electric current, contacted with a solution having a high pH or salt concentration, and the like, to liquefy or soften the intelligent and thereby release the gal pads from the first substrate and adhere the pads to the second substrate.

In one exemplary embodiment of this method of the invention, illustrated in FIG. 2, a system for creating gel pads on a first substrate and transferring the pads to an array format on a second substrate includes tape winding reels 10, 12 between which a tape 15 (e.g., a polystyrene tape) (first substrate) is passed. The tape can optionally be used for information storage, e.g., by coating with a conventional magnetic oxide layer. As the tape passes from the first tape reel 10 of the tape driver 23, it is guided along a tape path by guide wheel 20, past a gel pad dispenser (e.g., a nozzle, not shown, which deposits a solution of the gel monomer, which can be polymerized in situ) which deposits gel pads along the tape 15. The gel pads can optionally be washed, e.g., by spraying the pads with a buffer solution followed by air-drying, if desired. As the tape moves beyond the gel pad dispenser, each pad can be assayed by a quality control (QC) unit 27 to ensure the quality of the pads deposited (see infra and FIGS. 3 and 4). Defective pads are noted and the location stored and tracked, e.g., in a computer memory. The tape passes over a temperature-controlled head 30, which can be heated (or cooled) according to the properties of the gel pad employed. The temperature-controlled head 30 includes a heating/cooling element 28 for pad release and is connected to a Z axis servo 25. The tape head is controlled by a microcomputer which first ensures that the gel pad currently under the head is not defective; defective pads 24 are passed unchanged over the tape head and toward tape takeup reel 12, where they are collected. If the gel pad under the tape head is of acceptable quality, the microcomputer positions the tape head over the second substrate 40 (or moves the second substrate 40 under the tape head) to the correct location for the next pad in the array on second substrate 40. The tape head is then urged against second substrate 40 and the temperature is changed (e.g., the tip of the tape head is heated). In response to the change in temperature, the gel pad is dissociated from the tape 15 as the tape head is pressed against the surface of a second substrate 40, and the gel pad is transferred to the substrate 40. Used tape is collected past guide wheel 22 to takeup reel 12, and can be cleaned (e.g., to remove defective pads 24 and any residue) and reused for further array preparations.

Gel pads can be transferred from the first substrate in groups, e.g., in a row or rows, rather than one at a time, as illustrated above. Furthermore, the second substrate can also be a tape, rather than a rigid substrate; in this case, the second substrate tape could be urged against the first (tape) substrate by means of a roller or other tape transport mechanism. It will also be appreciated by the ordinarily skilled artisan, in light of the disclosure herein, that systems such as described herein can be used to effect the transfer of arrays of nucleotides (including, but not limited to DNA, RNA, and peptide nucleic acids) from one substrate to another, with or with concomitant transfer of a gel pad. Thus, for example, DNA can be transferred from one substrate to another, e.g., electrostatically, as described above.

Figure 3:
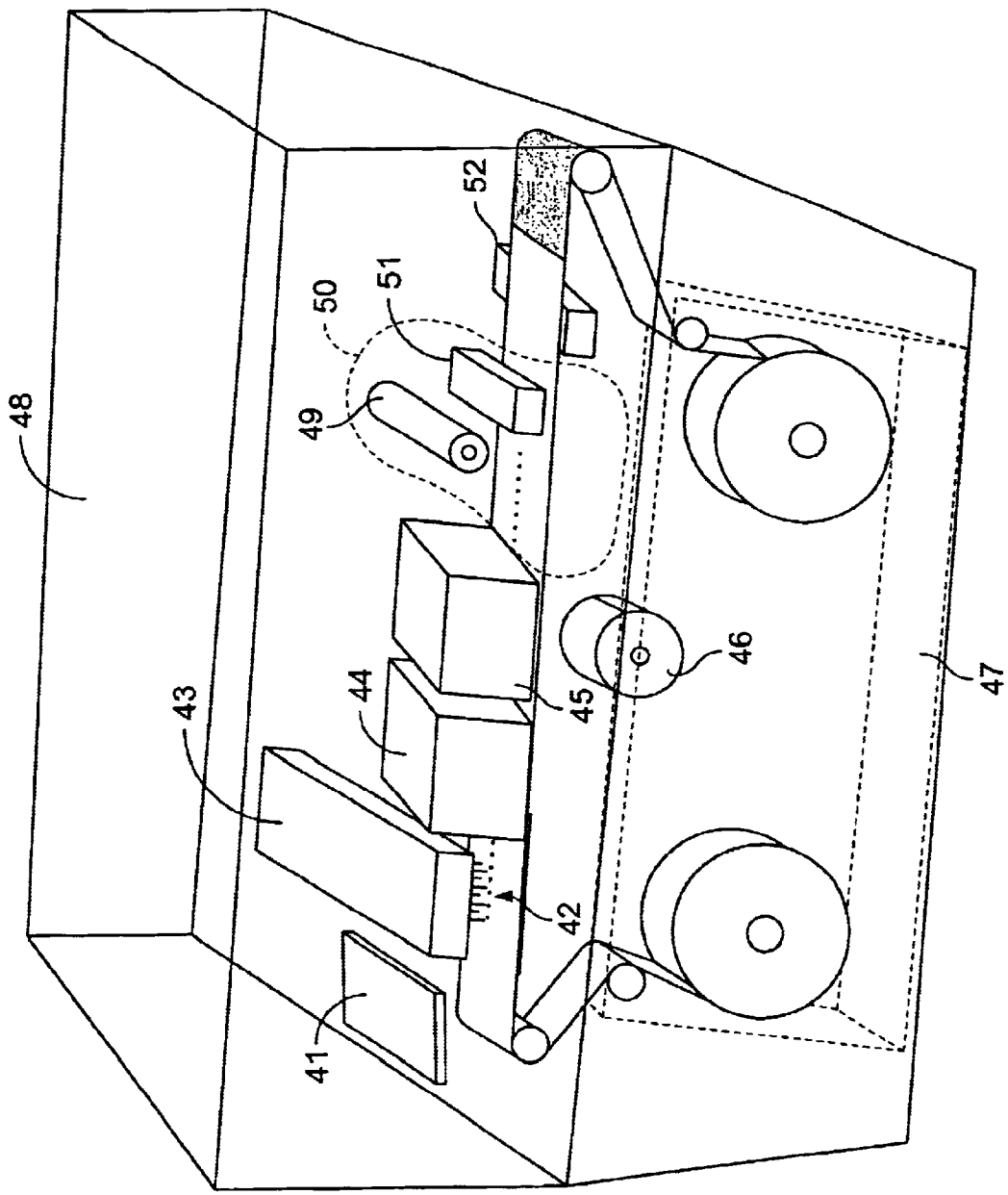
FIG. 3 depicts a system for manufacturing and testing a tape substrate with gel pads disposed thereon.
Figure 4:
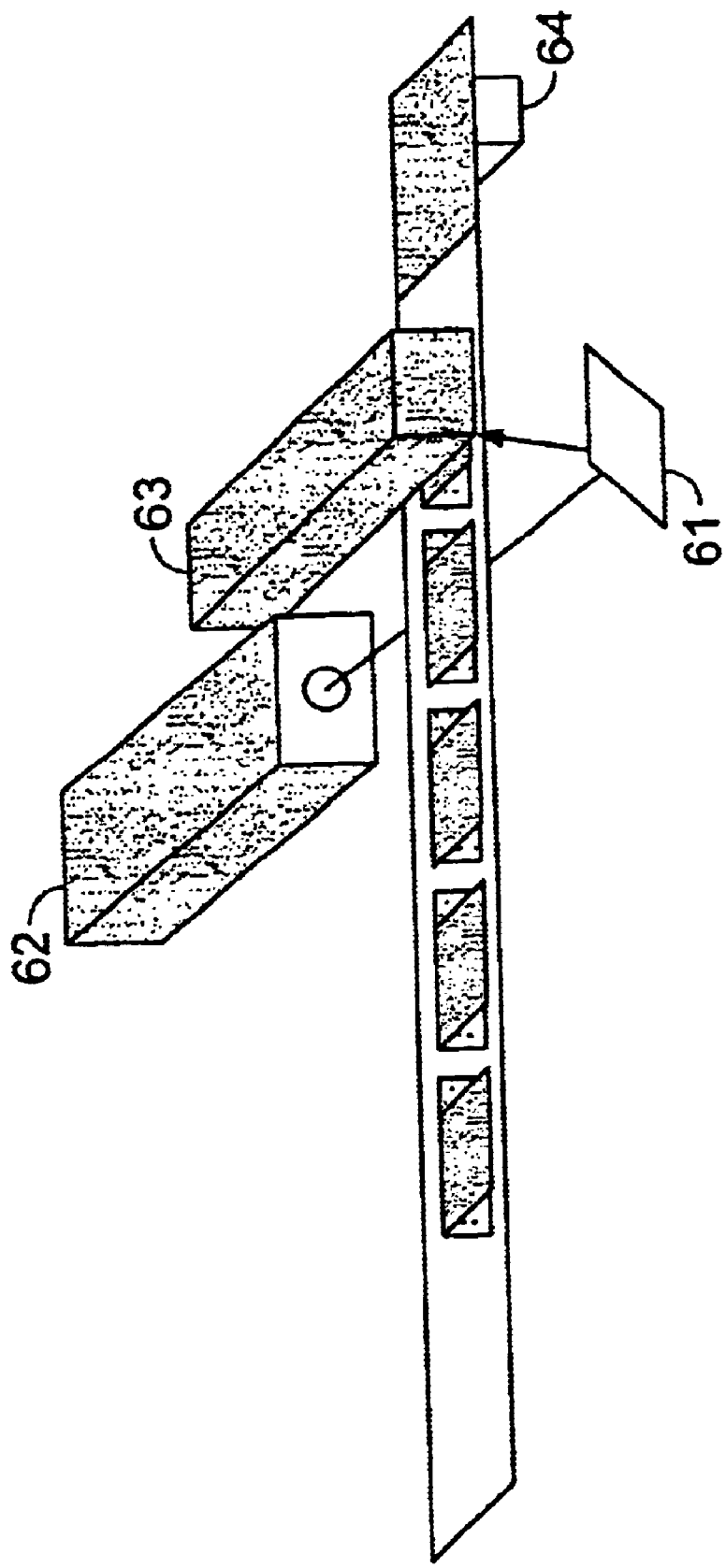
FIG. 4 depicts an imager for use in quality assurance of a tape substrate having gel pads deposited thereon. A high resolution 3-line color CCD (charged coupled device) 63 is mounted above the tape. The tape is incremented forward while the CCD scans the fluorescing gel arrays which have been excited by a laser 62 directed below the tape by a mirror 61. A selectable filter wheel for the laser could also be implemented. A magnetic read/write head 64 could be mounted for reading and writing data to the tape.
Figure 5:
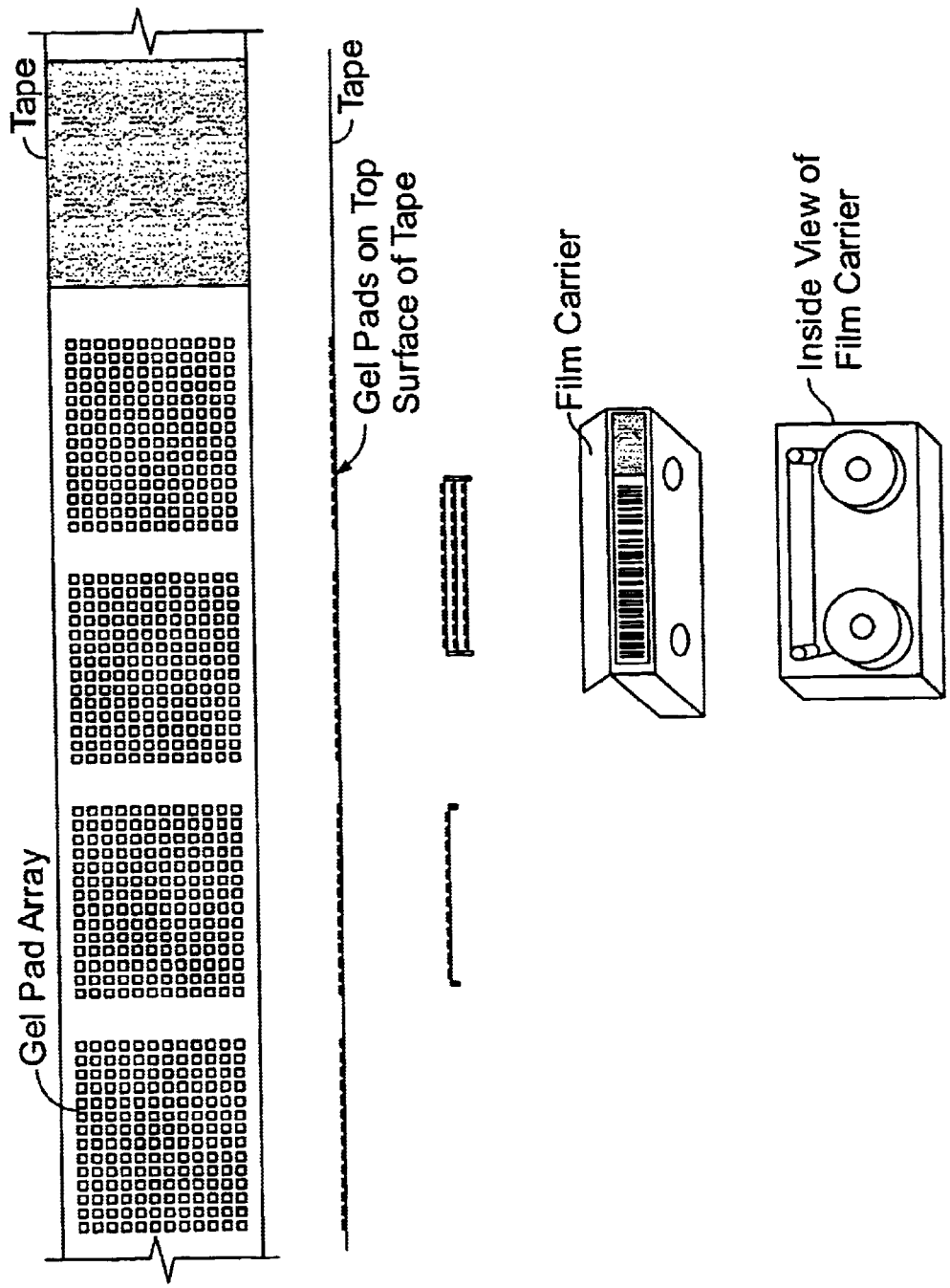
FIG. 5 depicts a tape (top, side, and end views) and a tape carrier. Gel pads are shown on the tope surface of tape. Acrylamide pads are adhered to the plastic in very high density arrays. Pads can be from 25 μm to 100 μm square and at spacing of 50 μm to 400 μm. The size and spacing of these space and array dimensions can be varied for a particular use or instrument. The film used is non-rigid transparent or translucent plastic which contains arrays of pads composed of acrylamide bound to surface of the tape. Sections of the film optionally are ferro-magnetic coated for magnetic storage of information. Optical encoding onto the film may also be employed by a series of marks and spaces manufactured into the edge of the film. The film has a barrier strip along each edge of the back of the film for sealing and spacing to prevent array compression and for tape handling. A film carrier is shown. The film carrier is a plastic enclosure for storage and insertion into an instrument. Bar coding on the edge of the carrier box is for cataloging. A cover closes over the end, covering the array film in the carrier.

A manufacturing system 48 for preparing a first (tape) substrate with gel pads deposited thereon is shown in FIG. 3. The system includes a sample holder 41 and tape reels 47. The reels serve to pass tape, at the urging of a precision stepper 46, under a dispenser (piezo-dispenser array 43), which provides pads 42 on the first substrate. The pads are polymerized at a polymerization station 44, followed by washing at a wash station 45 to remove impurities, unpolymerized monomers, and the like. The QA station 50 can include a spectrophotometric instrument 49 for determining the size, shape, and quality of the pads deposited on the substrate. In one embodiment, a charge-coupled device camera can be used to detect fluorescence, e.g., in response to a laser source, of a fluorescent molecule which is incorporated in the gel layer (and can optionally be removed at a later processing step, e.g., a second washing station). An exemplary imaging system 51 is shown in more detail in FIG. 4. If a magnetic layer is included in the tape substrate, the tape can be encoded by the magnetic encoding device 52 with information such as date of manufacture, location of defective pads, and the like. The tape is taken up on a take-up reel and stored for later transfer of the pads to an array on a second substrate, e.g., as described above. To prevent destruction of the pads as the tape is wound on the take-up reel, the tape can be ridged, for example as shown in the upper inset of FIG. 2, to prevent crushing of the pads.

In another embodiment, the first substrate can be a roller, e.g., a cylindrical element. Gel pads can be provided on the surface of the roller as the roller is rotated by a motor, the gel pads on the roller can be washed and assayed as described above. The gel pads are then transferred from the roller surface to the second substrate (which could be rigid or a flexible tape) as described above. After the gel pads are transferred to the second substrate, the roller surface as it rotates preferably passes through a cleaning apparatus. The roller surface can then be cleaned with each revolution to prevent contamination of gel pads with residue from preceding preparations. This system advantageously can provide continuous, rather than batch, operation.

The invention also provides multi-layered gel pad constructs. For example, in one aspect, the invention provides a gel pad which comprises at least two gel layers in contact with each other, e.g., a first gel layer on which is disposed a second gel layer, or first gel layer adjacent to and in contact with a second gel layer. A multi-layer gel pad of the invention can have two, three, four, or more layers, although greater numbers of layers will generally require more effort to prepare. The multi-layer gel pads of the invention can be configured to provide a variety of functions. For example, a first gel pad layer can include a polynucleotide (e.g., a probe for performing SBH) within the first gel matrix. A second gel layer can be disposed over and covering the first gel layer, the second gel layer can be a gel having an effective pore size small enough to prevent the diffusion of high-molecular-weight substances, such as proteins. The second layer thus serves as an effective barrier to prevent diffusion of substances, e.g., proteins, from a sample solution into the first gel layer, or from the first gel layer into solution. The multilayer gel pad can prevent interference from sample constituents, or can prevent the loss of valuable components from the first gel layer.

In another embodiment, a first gel layer can be formed with low ionic strength, e.g., an ionic strength lower than the ionic strength of a sample solution to be applied to the gel pad array. A second, protective or filtering gel layer covers and encapsulates the first gel pad layer. The low ionic strength of the first gel layer promotes osmotic movement of sample components into the first gel layer, thereby increasing the sensitivity of the first gel layer for a sample component of interest.

A multi-layer gel pad can be constructed by methods known in the art for the preparation of single-layer gel pads, or by the methods described herein. It will be appreciated that in certain embodiments, it is preferred to maintain registration between the layers of the multi-layer gel pad, e.g., in certain embodiments, it is preferred to place a second gel layer directly atop a first gel layer. The use of a mold or form can be useful in this embodiment, because molds can provide good registration between layers. A particularly useful method for preparing a multilayer gel pad array is the intelligent gel "molding" or "forming" layer methodology described above.

In still another embodiment, the invention provides gel pads which include living cells (referred to herein as "cell pads"). In one embodiment, the gel pad of the invention is a multilayered gel pad, having a first layer without cells, and second layer which includes cells (e.g., bacterial or eukaryotic cells). (Alternatively, cells can be grown on top of a gel layer, without being immobilized within a second gel layer). Exemplary embodiments are shown in FIG. 1 FIG. 1A depicts a first gel layer disposed adjacent a second, cell-containing gel layer. FIG. 1B depicts cells immobilized in a second gel layer which encapsulates a first gel layer. FIG. 1C shows cells maintained on the surface of a gel layer. The cells can be maintained in culture. This embodiment, provides a useful assay format for performing cell based assays in an array format. For example, the first gel layer could include detection means for detecting the presence (or absence) of a cell constituent (such as DNA) or a product of cellular metabolism (such as proteins, or products of transcription). For example, the cells in one layer can secrete molecules, such as growth factors, which can be monitored by the use of capture molecules in another layer of the multi-layer gel pad. The cells can also be lysed and cellular components measured. Thus, the response of the cells to a stimulus, such as addition of a growth factor, a toxin, a drug, or the like, can be monitored in a convenient and easily handled format.

Cell pads can also be configured to permit cells in one pad to secrete molecules which influence the growth of other cells in adjacent pads, e.g., an autocrine system. Thus, complex cell-based assays can be reduces to microscale format.

Gel-based reactious described herein can be performed with the gel immersed in an oil, e.g., paraffin oil.

Those skilled in the art will recognize, or be able to ascertain using no more than routine experimentation, numerous equivalents to the specific procedures described herein. Such equivalents are considered to be within the scope of this invention and are covered by the following claims.

The contents of all publications and patent applications described herein are hereby incorporated by reference.

Other embodiments are within the following claims.

What is claimed is:

1. A method of providing an array of gel pads having a substance disposed within, the method comprising:
   (1) providing a substrate on which is disposed the array of gel pads, and wherein said gel pads exist in an expanded and a contracted state;
   (2) contacting a gel pad of the array, while in the expanded state, with the substance, and allowing the substance to enter the expanded gel pad; and
   (3) causing the expanded gel pad to contract, wherein upon contraction molecules of the substance remain in the gel pad, thereby forming an array of gel pads having a substance disposed within.

2. The method of claim 1, wherein said substance is a nucleic acid.

3. The method of claim 1, wherein said substance is a cell.

4. The method of claim 1, wherein 1000 or more gel pads are disposed on said substrate.

5. The method of claim 1 wherein the gel pads comprise a plurality of layers.

6. The method of claim 1 wherein each layer of the plurality of layers is a different gel type.

7. The method of claim 6 wherein each layer contracts or expands in response to a different stimulus or to a different degree of a stimulus.

8. The method of claim 1 further comprising contacting a gel pad of the array, while in the expanded state, with a nucleotide and an enzyme, and allowing the nucleotide and the enzyme to enter the gel pad.

9. The method of claim 8 further comprising maintaining the array so that the enzyme adds a nucleotide to the nucleic acid.

10. The method of claim 1 wherein the gel pads contract exposure to a stimulus.

11. The method of claim 1 further comprising repeating steps (2) and (3).

12. The method of claim 1 wherein the array comprises voids.

13. The method of claim 12 wherein the voids are formed by exposing a gel portion to a laser source.

14. The method of claim 1 wherein the substrate is a flexible tape.

15. The method of claim 1 wherein the expanded state of the gel pads allow passage of a molecule up to 1000 times the molecular weight of the largest molecule able to passage in the minimized pore state.

16. A method of providing a gel having a living cell disposed within the gel comprising:
   (1) providing a substrate on which is disposed the gel, and wherein said gel can exist in an expanded and a contracted state;
   (2) contacting the gel, while in the expanded state, with the living cell and allowing the living cell to enter the gel;
   (3) causing the expanded gel to contract, wherein upon contraction the living cells remain in the gel, thereby forming a gel having a living cell disposed within.

17. The method of claim 16 wherein the gel is a component of an array of gels.

18. A method of providing a gel having a substance disposed within the gel comprising:
   (1) providing a flexible tape on which is disposed the gel, and wherein said gel can exist in an expanded and a contracted state;
   (2) contacting the gel, while in the expanded state, with the substance and allowing the substance to enter the gel;
   (3) causing the expanded gel to contract, wherein upon contraction the substance remains in the gel, thereby forming a gel having a substance disposed within.

19. The method of claim 8 further comprising repeating steps (2) and (3).

20. The method of claim 1 further comprising reacting the gel pad or the substance in the gel pad while the gel pad is in an expanded state.

21. The method of claim 1 wherein the expanded state of the gel pads allows passage of a molecule of at least 0.1 kilodaltons to enter the gel pad.

22. The method of claim 21 wherein the expanded state of the gel pads allows passage of a molecule of at least 1 kilodaltons to enter the gel pad.

23. The method of claim 22 further comprising hybridizing a nucleic acid in the gel pad.

24. The method of claim 20 wherein the substance is covalently attached to the gel pad.

25. The method of claim 16 wherein the living cell is a mammalian cell.

* * * * *